(12) United States Patent
Lutz

(10) Patent No.: US 6,650,725 B2
(45) Date of Patent: Nov. 18, 2003

(54) METHOD FOR REDUCING ARTIFACTS IN CT IMAGES THAT ARE CAUSED BY HIGH-DENSITY STRUCTURES

(75) Inventor: Andreas Lutz, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/201,697

(22) Filed: Jul. 24, 2002

(65) Prior Publication Data

US 2003/0026390 A1 Feb. 6, 2003

(30) Foreign Application Priority Data

Jul. 24, 2001 (DE) .......................... 101 35 994

(51) Int. Cl.$^7$ ................................. A61B 6/03
(52) U.S. Cl. ........................... 378/4; 378/901
(58) Field of Search .................. 378/4, 19, 910

(56) References Cited

U.S. PATENT DOCUMENTS

| 4,626,991 A | * 12/1986 | Crawford et al. ............. 378/4 |
| 4,709,333 A | 11/1987 | Crawford |
| 6,047,039 A | 4/2000 | Flohr |
| 6,263,096 B1 | * 7/2001 | Boag et al. ................ 382/128 |

FOREIGN PATENT DOCUMENTS

DE 19835451 3/1999

* cited by examiner

Primary Examiner—David V. Bruce
(74) Attorney, Agent, or Firm—Harness, Dickey & Pierce, P.L.C.

(57) ABSTRACT

A correction method is used for reducing artifacts caused by structures of high x-ray absorption in computer tomography images. By such a method, it is possible for interfering objects to be found both automatically and interactively in a computer tomography image. Relatively large interfering objects are preferably split up into a plurality of smaller interfering objects. The computer tomography image for each pixel of a selected image region is filtered as a function of its position relative to the interfering object.

30 Claims, 3 Drawing Sheets

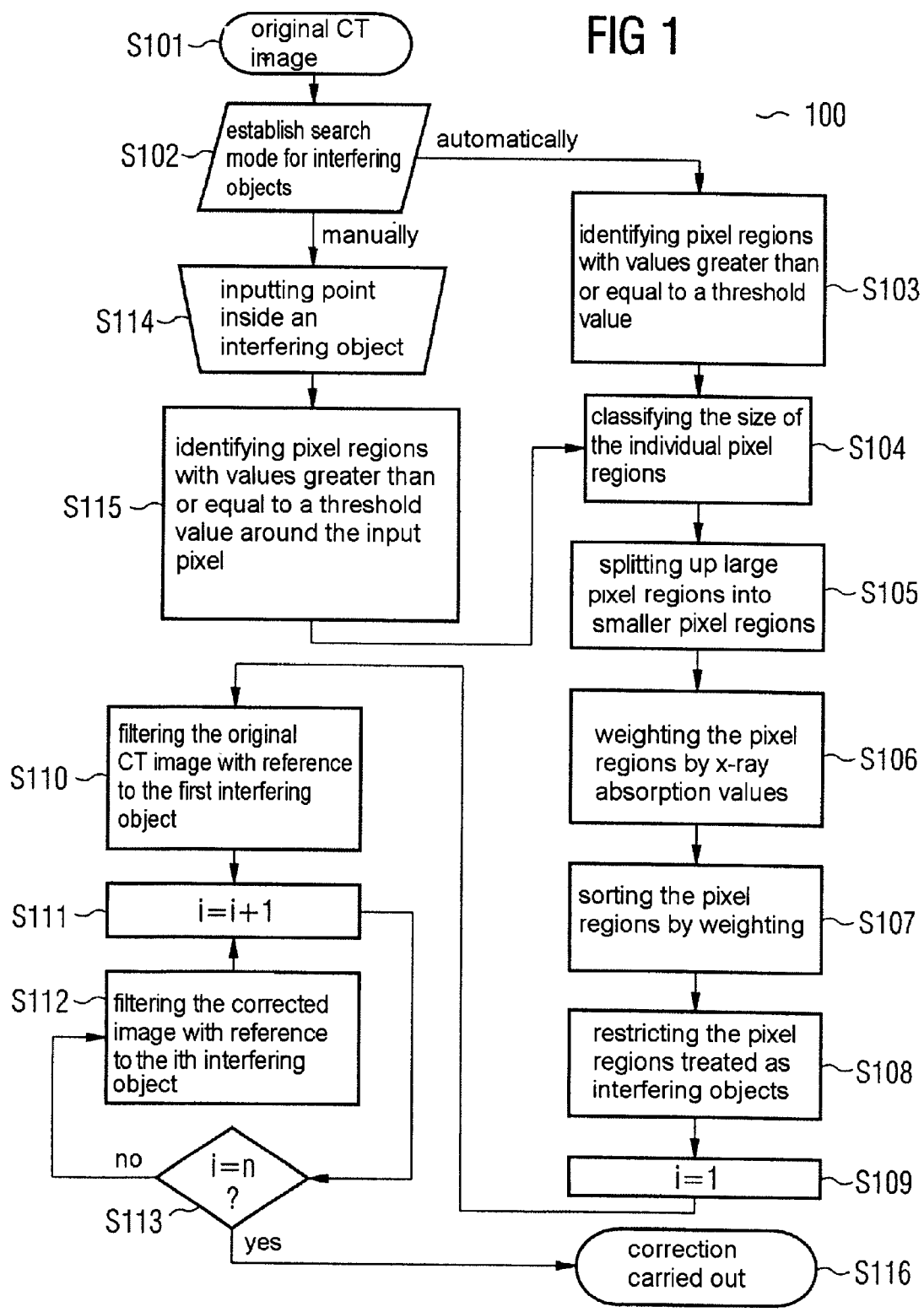

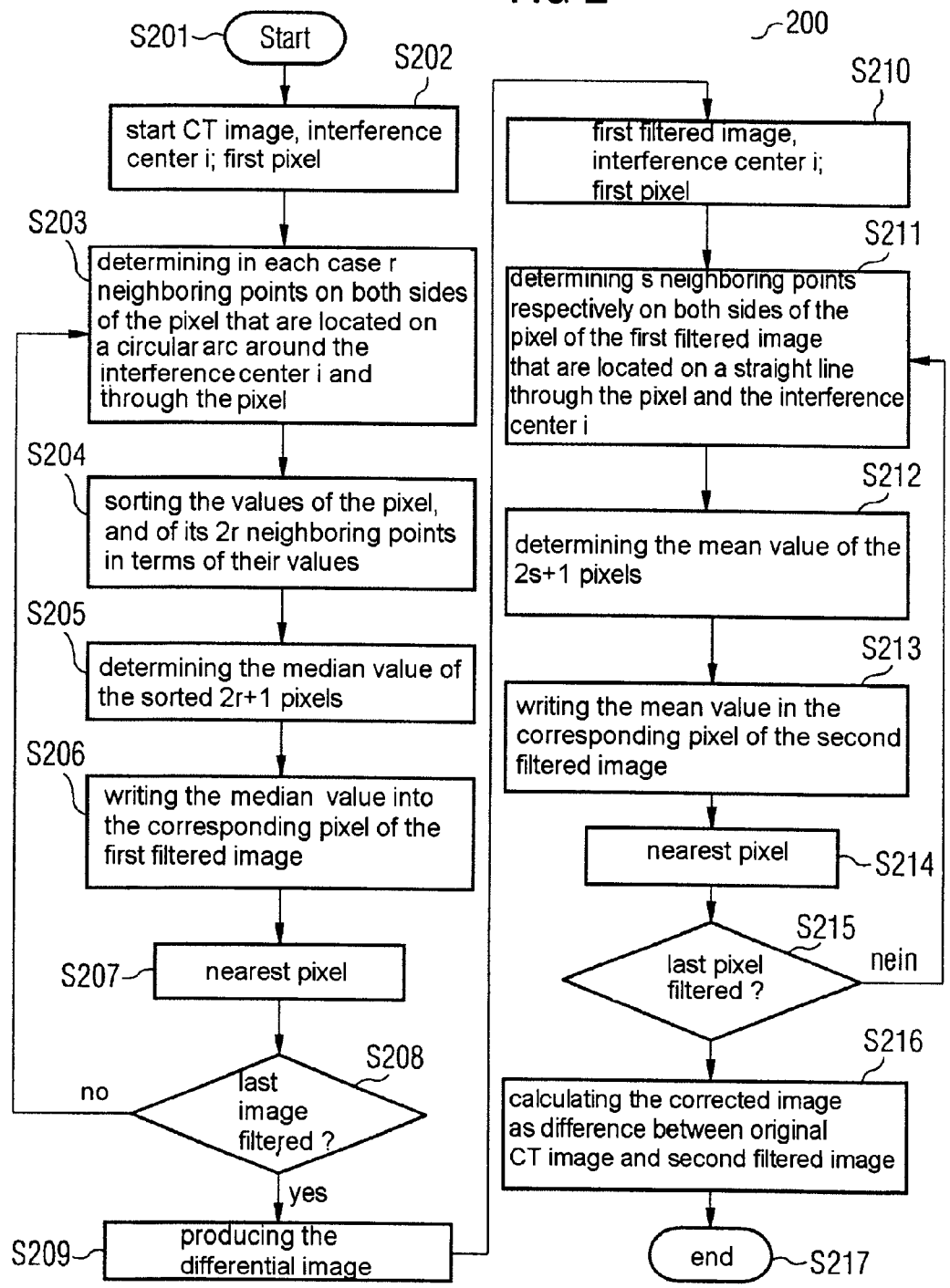

METHOD FOR REDUCING ARTIFACTS IN CT IMAGES THAT ARE CAUSED BY HIGH-DENSITY STRUCTURES

This application claims priority of German Patent Application No. 10135994.2, filed Jul. 24, 2001, the entire contents of which are hereby incorporated herein by reference.

FIELD OF THE INVENTION

The present invention generally relates to a method for executing a computer program for post-processing computer tomography images. In particular, it relates to a method for executing a computer program for image post-processing for reducing line artifacts that are caused by high-density structures in computer tomography images.

BACKGROUND OF THE INVENTION

If in the course of a computer tomographic (CT) examination, high-density objects are located in the scanning plane of the computer tomograph, the x-rays are absorbed so strongly by these objects that zones located in the shadow of these objects are now only transradiated by very weak x-radiation. Owing to the weak radiation, the signal-to-noise ratio is worsened for the examination regions in the shadow of the high-density objects, such that the values of the absorption coefficients for these regions can be determined only with relatively high uncertainty.

Given the presence of such high-density objects, it follows that artifacts, that is to say structures with nothing corresponding to them in the original, are to be observed in the CT images. Starting from the images of the high-density objects, these artifacts propagate like rays over the CT image. The image of such a high-density object in a CT image is denoted below as interfering object. In addition to metal objects such as, for example, belt buckles, metal clips or the like, it is frequently also tooth fillings or bone structures that are the cause of the described ray-shaped artifacts. Because of their ray-shaped nature, these artifacts are denoted as line artifacts. In the case of bone structures, the starting point of these line artifacts is formed in general by bone margins.

The cause of the line-like and ray-shaped course of the artifacts presides in the type of scanning of an original, to be examined, for creating a CT image.

The artifacts can sometimes determine the image to such an extent that they strongly impair, or even sometimes render impossible, a diagnostic analysis of the image. The attempt to eliminate the cause of the described line artifacts in the raw data supplied by a computer tomography examining instrument presupposes accurate knowledge of the imaging geometry of the examining instrument, and an enormous analytical outlay for minimizing the artifacts.

SUMMARY OF THE INVENTION

It is therefore an object of an embodiment of the present invention to specify a simple method and a computer software product for reducing line artifacts in CT images.

An object may be achieved by a correction method for reducing artifacts caused by structures of high x-ray absorption in computer tomography images that has steps for identifying an interfering object in a computer tomography image, for locating the interfering object in the computer tomography image, and for filtering the computer tomography image as a function of the position of selected pixels relative to the interfering object.

An object may be further achieved by a computer software product for reducing artifacts, caused by structures of high x-ray absorption in computer tomography images, for executing the above-described method on a data processing system with programmed instructions for executing on the data processing system.

A method according to an embodiment of the invention neither requires information on special structural features of the computer tomography examining instrument, nor is it dependent on the raw data created by a measurement. It advantageously reduces the artifacts in the finally reconstructed CT images.

An interfering object in a computer tomography image can be advantageously located by calculating the position of the centroid of the interfering object in this computer tomography image, such that the interfering object can be treated as a punctiform entity. Furthermore, to obtain improved filtering of a computer tomography image, it is advantageous to use all the pixels outside an interfering object for the purpose of filtering the computer tomography image. The filtering preferably extracts the instances of interference from the computer tomography image such that the corrected computer tomography image is advantageously obtained from the difference between the original computer tomography image and the filtered computer tomography image.

In accordance with an advantageous development, a computer tomography image can be filtered in two steps, in which case it is only neighboring pixels of a pixel to be filtered that are located on a circular arc around the centroid of the interfering object and through the pixel to be filtered that are included in a first filter-step, and it is only neighboring pixels of a pixel to be filtered that are located on the straight line through the pixel and the centroid of the interfering object that are included in a second filter step. It is thereby possible to make use transverse to the rays of the line artifacts of different filter criteria than in the direction of these line artifacts.

In order to be able to treat more simply complex artifact structures that emanate from extended interfering objects, large interfering objects are preferably split up into a multiplicity of smaller interfering objects.

It is advantageous to assign an interfering object only pixels with a gray-scale value or a color value that corresponds to an x-ray absorption value of at least 2000 Hounsfield units or more, such that the extent of the interfering objects in a CT image corresponds to the image of a corresponding high-density object.

Furthermore, in an advantageous way, given the presence of a plurality of interfering objects in a CT image, the interfering objects may be weighted in accordance with their x-ray absorption value for the correction method. The interfering objects may be sorted in accordance with the weighting, and starting with the first interfering object of the sorting sequence, the CT image for each individual one of the interfering objects may be corrected sequentially in accordance with the sorting sequence, a computer tomography image corrected with reference to a first interfering object of the sorting sequence forming the output for a further correction with reference to a second interfering object of the sorting sequence. In this case, the interfering objects are preferably sorted downward from a higher degree of x-ray absorption to a lower degree of x-ray absorption. Undertaking corrections of the instances of interference, caused by line artifacts in a CT image, separately for each individual interfering object permits the artifacts caused by the individual interfering objects to be eliminated specifically and individually, the largest line artifacts being reduced first by firstly performing the filtering of the CT image for interfering objects with a high degree of x-ray absorption.

It is possible with further advantage to restrict the number of the interfering objects to be used for filtering, such that only line artifacts that contribute substantially to the interference of the CT image are reduced.

The correction method according to an embodiment of the invention and the computer software product according to an embodiment of the invention for reducing artifacts caused by structures of high x-ray absorption in CT images can be applied for the purpose of image evaluation in computer tomography examining instruments and/or in systems for medical image processing. In particular, embodiments of the invention can be used in radiological diagnostics, for example for orthodontic examinations in which tooth fillings frequently cause line artifacts in the CT images. If these are not reduced, they greatly diminish the diagnostic value of a CT image.

BRIEF DESCRIPTION OF THE DRAWINGS

A particular embodiment of the method according to the invention is described below, reference being made to the following figures, of which FIG. 1 shows the flowchart of the method according to an embodiment of the invention, FIG. 2 shows the flowchart of the filter method of an embodiment of the present invention, FIG. 3b shows the image, corrected in accordance with the method according to an embodiment of the invention, of the pelvis of FIG. 3a.

DETAILED DESCRIPTION OF THE PREFERRED EMBODIMENTS

Figure 3A:
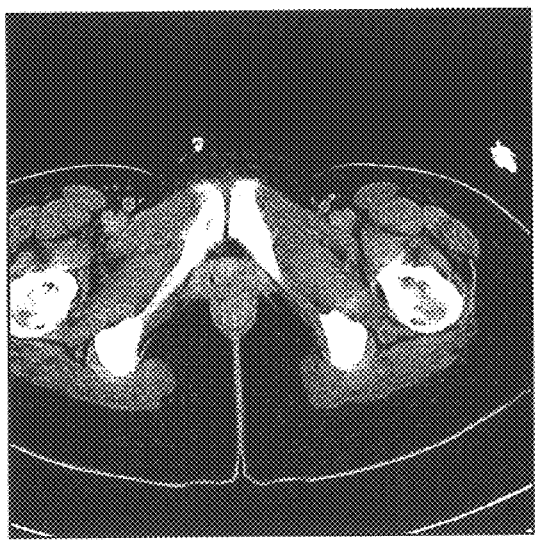
FIG. 3a shows a CT image of a pelvis with line artifacts.

The steps of the method according to an embodiment of the invention for reducing artifacts in CT images such as are caused by high-density structures are illustrated in FIG. 1. The method reduces the artifacts in the finally reconstructed image, and is therefore not dependent on the raw data supplied by a computer tomography examination. Required as preparation for correcting an image are the convolution kernel, that was used to reconstruct the image and is definitively responsible via the edge definition and/or edge smoothing for the sharpness, and the so-called "field of view". The described method has recourse, however, to none of the information that was used to reconstruct the CT image.

The method according to an embodiment of the invention can automatically determine interfering objects in a CT image, but interfering objects can also be located interactively by an operator in an entirely specific fashion. The method 100 illustrated in FIG. 1 begins with the provision 101 of the original CT image. A decision is taken in the subsequent step S102 as to whether interfering objects are to be identified automatically in the original CT image or whether an operator wishes to locate them specifically and interactively. In the case of selection of an automatic procedure, the method searches in step S103 for pixel accumulations and/or pixel regions of very high density that are treated as interfering objects. In the case of success, the centroid of the pixel region in the image plane is calculated for an identified interfering object.

Pixel regions of very high density are understood as accumulations of pixels whose gray-scale values or color values are greater than or equal to a prescribed threshold value. The depth of the representation of values of a pixel is usually 12 bits in the case of CT images. It is thereby possible to represent 4096 values in the form of gray levels or color values. In the case of CT images, the values of a pixel represent the absorption coefficient of the object under examination at the point represented by the pixel. The absorption coefficient is specified in Hounsfield units (HU), which express the x-ray absorption of a material relative to the x-ray absorption of water. Expressed in Hounsfield units water has an absorption value of 0 HU, air a value of –1000 HU and the maximum value of the system described by Hounsfield is 3000 HU. The range of the system described with the aid of Hounsfield units is therefore 4000 values, and so these values can all be represented in the 12-bit binary code. A dense bone, which can cause line artifacts in a CT image, typically has an absorption value of approximately 2000 HU and above.

In the case of the interactive method, an operator directly inputs the coordinates of an interfering object in step S114. The coordinates can be input by a mouse by clicking on a pixel inside an interfering object. Alternatively, the desired pixel can also be selected by using the arrow keys of the keyboard or by using other input aids. In the subsequent step S115, the pixel region whose individual pixels have values greater than or equal to the prescribed threshold value is then determined around the input coordinate in a way similar to that in step S103. An operator can now input further interfering objects in the CT image, and so the operation of steps S114 and S115 is repeated. The centroid of the object in the image plane is determined for each pixel region assigned to an interfering object in the case of the manually identified interfering objects, as well.

If the size of an interfering object exceeds a certain value, or if in this case it has an irregular shape, it can no longer be treated as a punctiform source of the line artifacts caused by it. Consequently, in step S104, the sizes of the identified interfering objects are classified, the interfering objects classified as large, which also include interfering objects with irregular structures, subsequently being split up into a plurality of partial interfering objects in step S105. In turn, the centroid in the image plane, the interference center, is calculated for each of the partial interfering objects.

In the subsequent step S106, the identified interfering objects are weighted by their x-ray absorption values, and sorted in accordance with this weighting in step S107. The number of the interfering objects to be used for correcting can be restricted in step S108, such that the CT image is corrected only for the artifact-relevant interfering objects. Step S109 initiates the filtering of the CT image. The first filtering of the CT image in step S110 is performed exclusively with reference to the first interfering object. It proceeds from the original CT image as the basis. If more than one interfering object is present, or if a plurality were selected for correction, a transition to further filter steps S112 is made in step S111. In these following filter steps S112, the CT image previously corrected for the preceding interfering object in each case forms the basis for the renewed filter process. Step S112 is repeated until it is established in the interrogation S113 that the image correction has been performed for all the interfering objects, or for all the selected ones. The resulting image of a preceding filter step in this case always forms the initial image for a filter step following thereupon. If the result of the interrogation in S113 is that the correction has been carried out for all interfering objects or for all selected ones, the correction method 110 is terminated in step S116.

The filter process 200 illustrated in FIG. 2 is of two-stage design. The first filter step uses an azimutal median filtering. It extends over the steps S202 to S208. The second filter step includes a radial averaging, and extends over the steps S210 to S215 of FIG. 2.

After the start of the filter process in step S201, the azimutal median filtering begins with the step S202 at a first pixel of the pixel regions selected for filtering, or of the selected regions of pixels. If the correction of the CT image refers to the first interference center, the first filter step begins with the original CT image as initial basis. In the case of subsequent corrections for further interference centers, the first filter step begins with the CT image respectively corrected for a preceding interference center.

In step S203, a determination is made of the neighboring points of the pixel to be filtered that are located on a circular arc around the interference center for which the filter operation is about to be undertaken. The pixel to be filtered is, of course, also located on this circular arc. An identical number of neighboring points on the circular arc are used for the filtering on both sides of the pixel to be filtered, and so together with the pixel to be filtered an odd number of pixels is always obtained.

In step S204, the pixels determined are sorted in the sequence of their color and gray-scale values, and the value of the mean pixel of this sorting sequence is subsequently determined in step S205 and written into a first filtered image.

The first filtered image has an identical number of pixels in conjunction with an identical ratio of horizontal to vertical pixels as the original CT image. The position of the pixel written into the first filtered image, or its coordinate, corresponds to the coordinate of the pixel to be filtered in the CT image used for the filter process as initial basis, and therefore also corresponds to the coordinate of the corresponding pixel in the original CT image.

The nearest pixel of the CT image used for the filter process as initial basis is used in step S207 for a further azimutal median filtering, and the steps S203 to S206 are applied repeated in the same way for this pixel as for the following ones.

If the last pixel of the selected image region has been filtered (S208), a differential image is produced in step S209 from the CT image used as initial basis and from the filtered image. In this case, differential image is understood to mean that the difference between the values of the corresponding pixels of the two images is formed in terms of image elements. When forming the difference, it is possible to undertake a restriction for positive values going upward and for negative values going downward, in order to restrict excessively massive changes to the original CT image at the end of the correction method. The differential image thus produced forms the result of the first filter step and is now the basis for the following radial averaging.

This begins in step S210 with the selection of a first pixel in the selected image region. From the latter, a specific number of neighboring points on a straight line through the pixel itself and the centroid of the interference center with reference to which the filter process is carried out are located in step S211. In each case, an identical number of neighboring points are determined on the side of the pixel facing the interference center and on the side of the pixel averted from the interference center. The values of the pixel and its neighboring points thus calculated are added in step S212, and the sum of the values that is thus formed is divided by the number of the pixels. The mean value calculated in this way is assigned in step S213 to a corresponding pixel in a second filtered image. As in the case of the first filtered image, in the case of the second filtered image, as well, both the number and the ratio of horizontal to vertical pixels are identical with the original CT image.

The process moves on successively to the remaining pixels of the selected image region via the steps S214 and S215, such that the radial averaging as it is characterized by the steps S211 to S213 is carried out sequentially for all the pixels of a selected image region. Obtained as a result is a second filtered image, which contains solely the result of the azimutal median filtering followed by filtering based on radial averaging.

In order to reduce the line artifacts in the original CT image, in the concluding step S216 the second filtered image is subtracted from the original CT image, and the result is stored either in the dataset of the original CT image, or as a dedicated dataset. In this case, subtraction is understood to mean that the difference between the values of corresponding pixels of the two images is formed pixel by pixel.

Step S217 terminates the filter method and leads back to the next step of the method according to the invention, as illustrated in FIG. 1.

Figure 3B:

Embodiments of the present invention can be used, inter alia, on computer tomography examining devices and systems for imaging processing of data obtained from computer tomography examinations or the like, as illustrated by FIGS. 3a and 3b. A tomographic image, created with the aid of computer tomography methods, of the pelvic region of an examined person is shown in FIG. 3a, it being possible to detect at the upper edge of the pubic region an interfering object of irregular extent with line artifacts that emanate therefrom and extend over a wide portion of the pelvic region. FIG. 3b shows the same tomographic image after application of the method according to the invention for reducing artifacts in CT images. The line artifacts that originally overlaid the actual image information are clearly reduced therein, neither the imaging of the interfering object itself nor other structures of the CT image having been impaired in any way at all by the method. The method according to the invention therefore constitutes a simple and effective method for reducing line artifacts in computer tomography images.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A correction method for reducing artifacts caused by structures of high x-ray absorption in computer tomography images, comprising the steps of:

identifying an interfering object in a computer tomography image;

locating the interfering object in the computer tomography image; and filtering the computer tomography image as a function of a position of selected pixels relative to the interfering object.

2. The correction method as claimed in claim 1, wherein an interfering object in a computer tomography image is located by calculating the position of a centroid of the interfering object in the computer tomography image.

3. The correction method as claimed in claim 1, wherein pixels outside an interfering object are used to filter the computer tomography image.

4. The correction method as claimed in claim 1, further comprising:
obtaining a corrected computer tomography image a difference between the original computer tomography image and the filtered computer tomography image.

5. The correction method as claimed in claim 1, wherein the step of filtering includes,
including locating only neighboring pixels of a pixel to be filtered on a circular arc around a centroid of the interfering object and through the pixel to be filtered in a first filter step, and
including locating only neighboring pixels of a pixel to be filtered on the straight line through the pixel and a centroid of the interfering object in a second filter step.

6. The correction method as claimed in claim 1, wherein large interfering objects are split up into a multiplicity of smaller interfering objects.

7. The correction method as claimed in claim 1, wherein only pixels with at least one of a gray-scale value and color value that corresponds to an x-ray absorption value of at least 2000 Hounsfield units are assigned to an interfering object.

8. The correction method as claimed in claim 1, wherein when there are a plurality of interfering objects in a computer tomography image, the interfering objects are weighted in accordance with their x-ray absorption value,
the interfering objects are sorted in accordance with the weighting, and
starting with the first interfering object of the sorting sequence, the computer tomography image for each individual one of the interfering objects is corrected sequentially in accordance with the sorting sequence, and wherein a computer tomography image corrected with reference to a first interfering object of the sorting sequence forms an output for a further correction with reference to a second interfering object of the sorting sequence.

9. The correction method as claimed in claim 8, wherein the sorting of the interfering objects is performed downward from a higher degree of x-ray absorption to a lower degree of x-ray absorption.

10. The correction method as claimed in claim 1, wherein a number of the interfering objects to be used for filtering is restricted.

11. A computer software product for reducing artifacts, caused by structures of high x-ray absorption in computer tomography images, for executing the above-described method as claimed in claim 1, on a data processing system with programmed instructions for executing on the data processing system.

12. The correction method as claimed in claim 2, wherein pixels outside an interfering object are used to filter the computer tomography image.

13. The correction method as claimed in claim 1, wherein all the pixels outside an interfering object are used to filter the computer tomography image.

14. The correction method as claimed in claim 2, wherein all the pixels outside an interfering object are used to filter the computer tomography image.

15. The correction method as claimed in claim 2, further comprising:
obtaining a corrected computer tomography image a difference between the original computer tomography image and the filtered computer tomography image.

16. The correction method as claimed in claim 3, further comprising:
obtaining a corrected computer tomography image a difference between the original computer tomography image and the filtered computer tomography image.

17. The correction method as claimed in claim 2, wherein the step of filtering includes,
including locating only neighboring pixels of a pixel to be filtered on a circular arc around the centroid of the interfering object and through the pixel to be filtered in a first filter step, and
including locating only neighboring pixels of a pixel to be filtered on the straight line through the pixel and the centroid of the interfering object in a second filter step.

18. The correction method as claimed in claim 4, wherein the step of filtering includes,
including locating only neighboring pixels of a pixel to be filtered on a circular arc around a centroid of the interfering object and through the pixel to be filtered in a first filter step, and
including locating only neighboring pixels of a pixel to be filtered on the straight line through the pixel and a centroid of the interfering object in a second filter step.

19. The correction method as claimed in claim 2, wherein large interfering objects are split up into a multiplicity of smaller interfering objects.

20. The correction method as claimed in claim 4, wherein large interfering objects are split up into a multiplicity of smaller interfering objects.

21. The correction method as claimed in claim 2, wherein only pixels with at least one of a gray-scale value and color value that corresponds to an x-ray absorption value of at least 2000 Hounsfield units are assigned to an interfering object.

22. The correction method as claimed in claim 4, wherein only pixels with at least one of a gray-scale value and color value that corresponds to an x-ray absorption value of at least 2000 Hounsfield units are assigned to an interfering object.

23. The correction method as claimed in claim 2, wherein when there are a plurality of interfering objects in a computer tomography image, the interfering objects are weighted in accordance with their x-ray absorption value,
the interfering objects are sorted in accordance with the weighting, and
starting with the first interfering object of the sorting sequence, the computer tomography image for each individual one of the interfering objects is corrected sequentially in accordance with the sorting sequence, and wherein a computer tomography image corrected with reference to a first interfering object of the sorting sequence forms an output for a further correction with reference to a second interfering object of the sorting sequence.

24. The correction method as claimed in claim 4, wherein when there are a plurality of interfering objects in a computer tomography image, the interfering objects are weighted in accordance with their x-ray absorption value,
the interfering objects are sorted in accordance with the weighting, and
starting with the first interfering object of the sorting sequence, the computer tomography image for each individual one of the interfering objects is corrected sequentially in accordance with the sorting sequence, and wherein a computer tomography image corrected with reference to a first interfering object of the sorting sequence forms an output for a further correction with reference to a second interfering object of the sorting sequence.

25. The correction method as claimed in claim 23, wherein the sorting of the interfering objects is performed downward from a higher degree of x-ray absorption to a lower degree of x-ray absorption.

26. The correction method as claimed in claim 8, wherein the sorting of the interfering objects is performed downward from a higher degree of x-ray absorption to a lower degree of x-ray absorption.

27. The correction method as claimed in claim 2, wherein a number of the interfering objects to be used for filtering is restricted.

28. The correction method as claimed in claim 4, wherein a number of the interfering objects to be used for filtering is restricted.

29. The correction method as claimed in claim 8, wherein a number of the interfering objects to be used for filtering is restricted.

30. The correction method as claimed in claim 9, wherein a number of the interfering objects to be used for filtering is restricted.

* * * * *